US006828576B2

(12) United States Patent
Spivak

(10) Patent No.: US 6,828,576 B2
(45) Date of Patent: Dec. 7, 2004

(54) UV LED LIGHT PROJECTION METHOD AND APPARATUS

(76) Inventor: Paul Spivak, 32251 Walker Rd., Avon Lake, OH (US) 44012

( * ) Notice: Subject to any disclaimer, the term of this patent is extended or adjusted under 35 U.S.C. 154(b) by 0 days.

(21) Appl. No.: 10/633,920

(22) Filed: Aug. 4, 2003

(65) Prior Publication Data

US 2004/0075065 A1 Apr. 22, 2004

Related U.S. Application Data

(60) Provisional application No. 60/477,685, filed on Jun. 11, 2003.

(51) Int. Cl.$^7$ ................................................ A61N 5/00
(52) U.S. Cl. ............................. 250/504 R; 250/494.1; 250/493.1; 250/461.1; 250/365; 257/88; 257/98
(58) Field of Search .......................... 250/504 R, 494.1, 250/493.1, 461.1, 365; 257/88, 98

(56) References Cited

U.S. PATENT DOCUMENTS

| 6,447,537 | B1 | * | 9/2002 | Hartman ...................... 607/94 |
| 6,452,217 | B1 | * | 9/2002 | Wojnarowski et al. ........ 257/99 |
| 6,621,211 | B1 | * | 9/2003 | Srivastava et al. .......... 313/503 |
| 2002/0074559 | A1 | * | 6/2002 | Dowling et al. ............... 257/99 |
| 2003/0216795 | A1 | * | 11/2003 | Harth et al. ................... 607/88 |

OTHER PUBLICATIONS

U.S. patent application in the name of Fiset Ser. No. 10/714/824, filed Nov. 17, 2003, based upon provisional application priority date of May 24, 2003.

* cited by examiner

Primary Examiner—Nikita Wells
(74) Attorney, Agent, or Firm—Patrick J. Daugherty; Driggs, Lucas, Brubaker & Hogg Co. LPA

(57) ABSTRACT

A light emitting diode projection apparatus and method is provided for irradiating a subject with ultraviolet radiation, comprising a plurality of light emitting diodes configured to emit ultraviolet radiation and arranged in a matrix, and a power modulation control unit in communication with the diodes. The power modulation control unit is configured to energize and cause the diodes to emit light and thereby irradiate the subject with ultraviolet radiation sufficient to cause material physical change in the subject. In one embodiment of the invention, the material physical change is skin tanning. The amount, intensity, duration and type of UVR projected by the plurality of UV LED's may be varied by the power modulation control unit responsive to information input into the power modulation control unit.

18 Claims, 2 Drawing Sheets

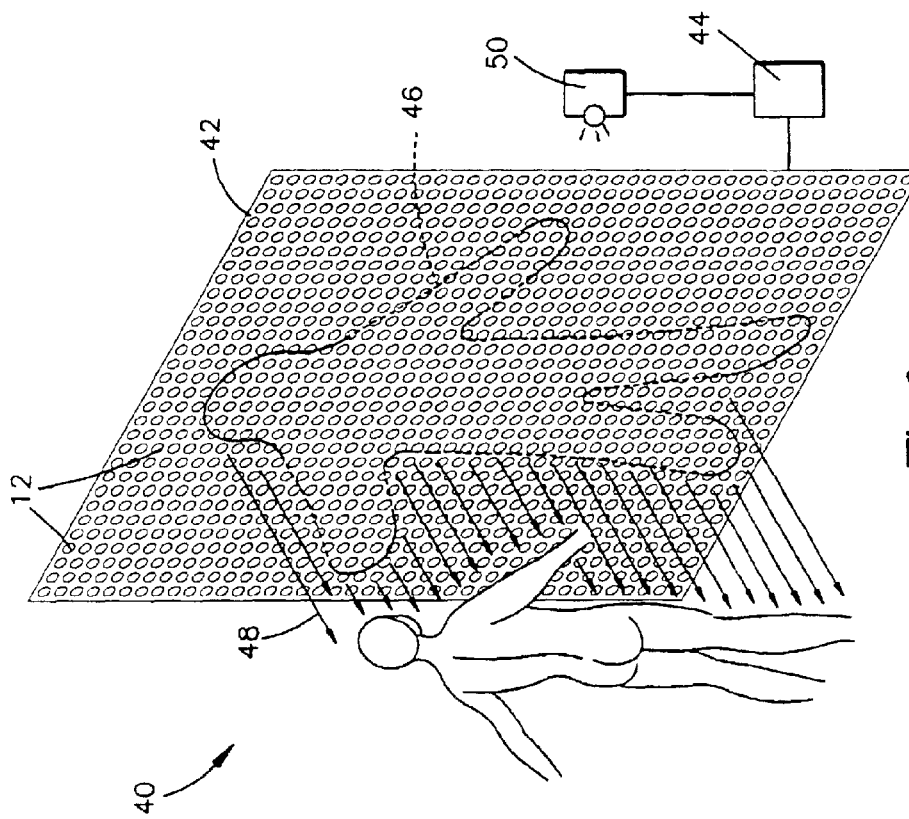
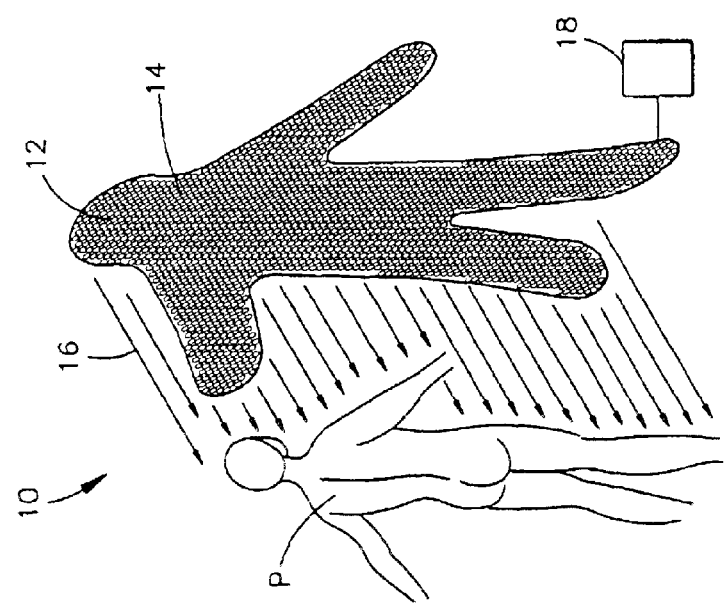
Fig.1
Fig.2

UV LED LIGHT PROJECTION METHOD AND APPARATUS

CROSS REFERENCE TO RELATED APPLICATION

This application claims the benefits of provisional patent application Ser. No. No. 60/477,685, filed Jun. 11, 2003.

FIELD OF THE INVENTION

The present invention provides a method and apparatus for projecting ultraviolet light through man-made energy and illumination sources. More particularly, the present method and apparatus provide for skin tanning through the use of a plurality of ultraviolet light emitting diodes (LED's) in combination with a power modulation circuit.

BACKGROUND OF THE INVENTION

All human beings need and crave sunlight. In particular, virtually everybody desires the warm and pleasant sensation associated with sunlight. One desired side effect of exposure to strong sunlight is the "tanning" effect upon human skin. Tanning occurs when the skin produces additional pigment (coloring) to protect itself against burning from ultraviolet radiation (UVR) present within sunlight. Ultraviolet radiation, sometimes also called ultraviolet light, is invisible electromagnetic radiation of the same nature as visible light, but having shorter wavelengths and higher energies.

When strong, naturally occurring sunlight is not obtainable, projecting man-made UV light upon human skin is a desirable substitute. "Tanned" skin is generally considered physically attractive, and a large market exists to serve people with artificially generated UV lighting systems that will provide a tanning effect in the absence of natural sunlight. Other benefits associated with the reception of UV radiation is the production of vitamin D by the skin; and the prevention of depression and other "seasonal affective disorders" (SAD's) during the dark winter months in locations distant from the equator. Accordingly, millions of people seek ways to enjoy ultraviolet light and, in particular, to keep their skin tanned, in the absence of naturally occurring strong sunlight.

Prior art tanning "beds" and "booths" are well-known, popular devices that utilize rows of fluorescent lighting tubes to project UVR upon a person in order to cause the person's skin to tan. These are particularly popular in northern regions of the United States, where strong sunlight is not available during the fall and winter months. A typical prior art fluorescent lighting tube tanning bed or booth forms an enclosure about a person being tanned. Once inside the prior art bed or booth, a person is surrounded by a plurality of fluorescent tubes arranged in rows or other configurations that are intended to directly or indirectly illuminate a person's exposed skin.

The use of UVR fluorescent tubes has a number of significant disadvantages. They have large power requirements, resulting in high energy costs for systems utilizing them. They also emit large amounts of heat, resulting in needless heat exposure for UVR fluorescent tube system users.

It is also preferable to keep the distance between the skin and each of the plurality of tubes within a more or less common range. Otherwise, skin that is closer to the fluorescent tubes will receive more UVR and, thus, tan or suffer erythema (burn) quicker than skin positioned farther away. Designing tanning beds or booths of fluorescent lighting tubes that assure a uniform distance between a person's skin and the fluorescent tubes is problematic. The arrangement of fluorescent tubes is generally restricted by the long linear shape of the fluorescent tubes. Since body shapes are not linear, a person aligned more or less parallel to a bank of fluorescent tubes will necessarily have some skin regions much closer to the tubes (for example, the tip of the nose) than others (such as the intersection of the bottom of the neck in the top of the chest).

Moreover, in order to avoid undesirable gaps in illumination projection, generally the fluorescent tubes must be as long as the person receiving illumination. Therefore, the selection of UVR fluorescent tubes for the typical prior art tanning bed or booth is generally limited to long tubes arranged in rows. This results in large inefficiencies in energy utilization and fluorescent lighting requirements, wherein generally rectangular regions much larger than the general human profile must be illuminated by the fluorescent tubes.

UVR fluorescent lighting tubes also present problems with providing a consistent energy output profile. The typical fluorescent lighting tube is designed to emit a uniform and predictable amount of UVR. As the lighting tube ages, the amount of UVR emitted starts dropping off and, therefore, the effective tanning produced drops off. This UVR output drop-off is not apparent to an operator of the tanning bed or booth, or to a person using the tanning bed or booth, unless it is observed through less effective tanning or longer illumination times required to achieve the same relative tanning effect. Therefore, tanning booth or bed operators must keep track of the hours of service of a UVR fluorescent tube, and regularly replace the tubes at the end of a predicted service-hour life. As a result, perfectly good UVR fluorescent tubes are needlessly discarded, resulting in a huge and costly inefficiency throughout the UV tanning industry.

It has also become recently known in the tanning industry that the type of UV light is very important. In the electromagnetic spectrum, UVR extends between the blue end of the visible spectrum and low-energy X-rays, straddling the boundary between ionizing and non-ionizing radiation (which is conventionally set at 100 nm). Ionizing radiation, such as X-rays and gamma-rays, have enough energy to ionize (i.e. break up) atoms. Non-Ionizing radiation, such as visible light, microwaves, or radio waves, do not.

The frequency of electromagnetic fields is measured in Hz (hertz), or cycles per second, where 1 kHz (kilohertz)=1000 cycles/second. UVR is conventionally divided into three bands in order of increasing energy: UVA, UVB and UVC. This division corresponds broadly to the effects of UVR on biological tissue. The wavelength ranges in nanometers and common names of the UVR bands are:

UVA: 315–400 nm "Black light"
UVB: 280–315 nm "Erythemal UV"
UVC: 100–280 nm "Germicidal UV"

Due to their different wavelengths and energies, each of these bands has distinct effects on living tissue. The highest energy band, UVC, can damage DNA and other molecules and is often used as a germicidal agent. UVC is rapidly attenuated in air and, therefore, it is not found in ground-level solar radiation. Exposure to UVC, however, can take place close to sources, such as welding arcs or germicidal lamps. UVB is the most effective UV band in causing tanning and sunburn (erythema) and it can affect the immune system. Although UVA is the least energetic UV band, and much less effective than UVB in causing erythema and tanning, it can cause these effects at levels present out-of-doors. UVA penetrates deeper in the skin due to its longer wavelength and plays a role in skin photoaging. UVA can also affect the immune system.

Because of a large difference in the efficiency of each UVR wavelength in causing biological damage, UVR exposure and dose are computed as weighted values. Each wavelength is assigned a weight according to its effectiveness in producing erythema or keratoconjunctivitis. The exposure thus calculated is called "effective irradiance" and the dose, "biologically effective dose."

The main source of natural ultraviolet radiation is the sun. Most of the solar radiation reaching the surface of the earth is infrared radiation (55%) and visible light (40%). Approximately 5% of the ground-level solar radiation is ultraviolet radiation, mostly in the UVA range. Solar UVR varies strongly with season, time of day, latitude and atmospheric conditions, generally reaching a daily peak around solar noon and a yearly peak in summer. UVB levels change rapidly with time of day while UVA levels vary more slowly throughout the day. UVB is strongly absorbed by stratospheric ozone, so depletion of this protective layer results in higher UVB intensity at ground level. Exposure to solar radiation at noon in mid-latitudes, during spring and summer, routinely exceeds the threshold for damage to the eyes and skin within a few minutes.

In addition to solar UVR, which represents the main exposure to UVR for the majority of the population, there are a variety of artificial sources of UVR. Electric welding arcs are strong sources of ultraviolet radiation, and can produce acute overexposure to UVR within a radius of several meters in just a few seconds. Arc lamps, used in some specialized projection and illumination, and in the printing industry, can also be strong sources of ultraviolet radiation. Curing lamps use UVR to harden resins and to dry paints and other substances; they can be quite intense, and are usually located inside enclosed cabinets. "Black lights" are UVA lamps used for non-destructive testing, insect control, and in the entertainment industry. Germicidal lamps, commonly used for sterilization in hospitals, are strong emitters of UVB and UVC radiation. Therapeutic UVR lamps, used in physiotherapy and dermatology for the treatment of psoriasis and other skin conditions, can emit either UVA or UVB.

Studies suggest that children and adolescents may be tanned or burned more by equivalent amounts of UVB rays than adults. Common sunscreens are designed to filter out UVB rays. In contrast, longwave UVA rays do not greatly impact the outer skin layers and are less likely to cause burning than UVB rays. By penetrating deeper into skin layers and still generating a tanning effect, without burning or damaging the upper skin layers, UVA rays are considered by many to be a safer alternative to UVB rays. Accordingly, the typical prior art UVR tanning systems emit mostly UVA radiation with a few percent content of UVB, and their use can lead to significant exposures to UVA radiation. However, while UVA is less effective than UVB in causing erythema, it penetrates deeper in the skin, contributing to premature aging and other health effects, including carcinogenesis.

Moreover, the reaction of any one person's skin to either type of UV lighting system is dependent upon the person's skin type. In general, people with darker skin complexions can receive more UVB light without burning or suffering upper skin layer damage. Such a person may prefer UVB light over UVA light for its more rapid and, therefore, more time-efficient tanning effect. In contrast, people with extremely fair skin complexions may burn readily from even limited UVB exposure, and may not be able to effectively tan at all. They may wish to utilize only UVA lighting for other beneficial health effects. The majority of people using UV lighting systems will fall between these two extremes. Accordingly, each person may benefit from an individualized relative percentage UVA to UVB light rays, received over their own individual optimal exposure time frames. Prior art UVR fluorescent lighting systems typically emit only one constant UVA/UVB profile. The relative relation of UVA to UVB cannot be varied and still project an effective composite tanning UVR.

What is needed is a new and improved artificial UV lighting system and method that provides a means for more uniformly illuminating the human body, wherein the artificial lights used maintain a generally uniform distance from all of the exposed skin and, therefore, all of this exposed skin may receive the same relative UV lighting strength. What is also needed is a way to more efficiently conform the yield of the light illumination sources to the shape of the human body. What is also needed is a way to efficiently provide a reliable and predictable UV illumination output, one that does not require needlessly disposing of expensive lighting sources. Is also desirable to provide a method and system wherein the type of UV radiation may be selected; for example, wherein UVA, UVB, or other light radiation spectrums, or a blend of any of these spectrums may be selected and, more preferably, where the relative percentages a UVA and UVB and/or their relative intensities may be varied over time, dependent upon an individual's needs.

SUMMARY OF THE INVENTION

A light emitting diode projection apparatus and method is provided for irradiating a subject with ultraviolet radiation, comprising a plurality of light emitting diodes configured to emit ultraviolet radiation and arranged in a matrix, and a power modulation control unit in communication with the diodes. The power modulation control unit is configured to energize and cause the diodes to emit light and thereby irradiate the subject with ultraviolet radiation sufficient to cause material physical change in the subject. In one embodiment of the invention the material physical change is skin tanning. The amount, intensity, duration and type of UVR projected by the plurality of UV LED's may be varied by the power modulation control unit responsive to information input into the power modulation control unit.

BRIEF DESCRIPTION OF THE DRAWINGS

FIG. 1 is a perspective illustration of a LED UV projection system according to the present invention.

FIG. 2 is a perspective illustration of another LED UV projection system according to the present invention.

DESCRIPTION OF THE INVENTION

Figure 5:
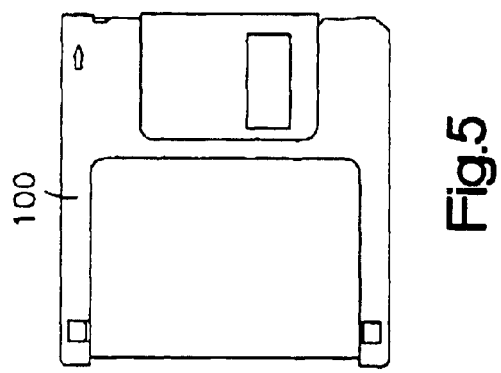
FIG. 5 is an article of manufacture comprising a computer usable medium having a computer readable program according to the present invention embodied in said medium.

The present invention provides for a UV light emitting diode (LED) system and method. As is well-known in the art, LED's have generally small and round physical characteristics. Accordingly, a plurality of LED's can be arranged into matrixes of virtually any type of shape. Referring now to FIG. 1, an LED UV projection system 10 according to the present invention is illustrated. A plurality of LED's 12 is arranged into a matrix 14 that closely follows a human profile shape. When energized by a power and control system 18 the matrix 14 projects a composite UV light illumination pattern 16 that generally follows its human profile shape. It is preferred that the matrix 14 shape conform to the intended target of the UV illumination pattern 16, a user P. In this fashion the present embodiment provides superior efficiencies compared to prior art fluorescent tube tanning systems, which necessarily consist of generally rectilinear arrays of long linear fluorescent tubes.

Alternatively, another embodiment of an LED UV projection system 40 according to the present invention is illustrated in FIG. 2. A generally rectangular array 42 of LED's 12 is arranged in a fashion similar to a typical array of fluorescent UV lighting tubes as found in a prior art tanning bed or booth. What is new is that the power and control system 44 selectively fires only those LED's 12 necessary to illuminate a particular individual P: therefore those LED's 12 within the profile pattern 46 are energized to emit UVR 48.

The array of LED's may be in communication with a sensor system 50 that detects shape parameters of the person P and determines the profile pattern 46 according to those parameters. For example, those LED's 12 located beyond the height and/or width of the person may not be illuminated. Thus, the replacement of UV fluorescent tubes with UV LED's allows for superior lighting efficiencies, since no energy or lighting resources must be expended to illuminate regions beyond the human profile shape 46.

Figure 3:
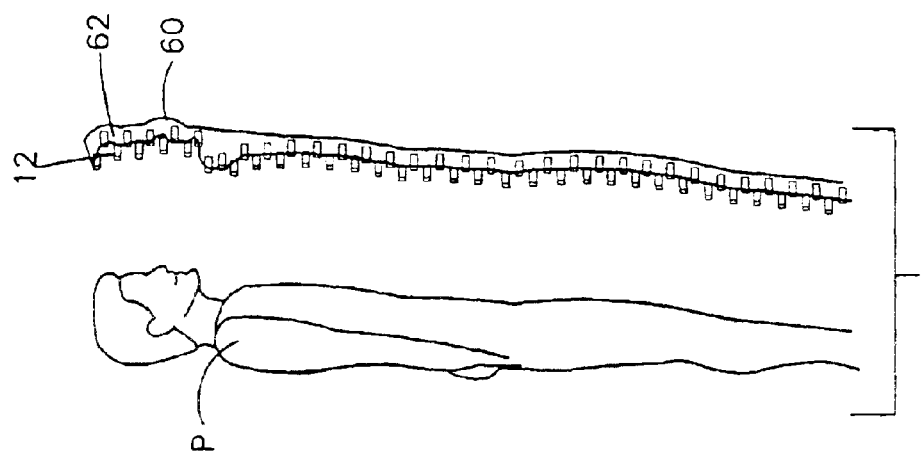
FIG. 3 is a side perspective illustration of a LED UV projection system according to the present invention.

Another advantage will be really apparent in that a matrix of LED's arranged to conform to human profile need not be planar, but may undulate to conform to the curves and shape of a human body. FIG. 3 provides a side view of one embodiment of the present invention wherein UV LED's 12 are arrayed in a mounting structure 60 with a shape corresponding generally to the shape of a user P. In general, the amount of effective radiant energy received from artificial UV lighting is dependent upon the distance of skin from the lighting device, wherein the energy received is reduced in inverse proportion to an increase in distance. Therefore, the person aligned before an array of prior art linear UV fluorescent tubes will receive more energy upon those portions of skin closer to the tubes (such as the tip of the nose) relative to other skin portions. Thus, a more uniform LED-to-skin distance may be maintained by designing a matrix to correspond to a typical three-dimensional human body shape, in contrast to the limitations inherent in the tubular shape of the UV fluorescent tubes utilized in the prior art tanning bed and booths. For eliminating facial regions, the LED's can be more or less recessed in a shape 62 conforming to the shape of a human head and face. The structure 60 may also be formed from a flexible media with a good physical memory, such as an elastomeric compound structure. This would allow the structure 60 shape to be formed and reformed to conform to each individual user.

UV LED's also require far less power than UV fluorescent tubes, and emit far less heat than UV fluorescent tubes. Thus, a UV tanning system according to the present invention has superior energy efficiencies, resulting in significant economic savings, and also far less demand upon electrical utility systems. The present invention thereby enables savings of the natural resources required to generate electricity, and indirectly reduces pollution generated in supplying the energy requirements, in contrast to prior art UV fluorescent tube tanning systems.

An important advantage of UV LED's over UV fluorescent lighting tubes is the consistent UV light output inherent in a UV LED device. Unlike the much larger UV fluorescent lighting tube, which suffers a degradation of efficiency and light output over the course of its life, the much smaller UV LED emits a constant and predictable amount of UV LED light over the course of its service life, which is itself significantly longer than that of a UV fluorescent lighting tube. Therefore, the present invention provides for a tanning bed or booth comprising a lighting source with a significantly longer service life. The present invention also thus provides for significant savings in the cost of light source replacement and in the man-hours required to service the equipment to keep the UV light projection system performing at an acceptable and predictable level.

Another important advantage of the present invention is that the amount and type of UV light rays emitted by a matrix of UV LED's can be easily controlled through a power and control system that may selectively energize individual UV LED's. Thus, a matrix of UV LED's may comprise a blend of UVA and UVB LED's into virtually any type of configuration. An LED matrix may have a one-for-one blend of alternating UVA and UVB LED's, or other combinations may be desirable, such as providing for two or three UVA LED's for every UVB LED. It is to be understood that these proportions are illustrative only, and it will be readily apparent to one skilled in the art that different combinations, or even a blending of different combination levels, may be desirable to practice the present invention. In the present invention, all of the LED's may be selected and, therefore, the matrix may have a constant output of UVA, UVB, or blend of UVA and UVB light. Alternatively, the power and control system may be programmed to provide for different combinations of UVA and UVB illumination, allowing a user to select different relative percentages of UVA and UVB LED's, or even selecting only one of the UVA and UVB LED pluralities.

Another advantage of the present invention is that the power and control system utilized to energize the UV LED's is programmable to provide for specific illumination intensities and periods. The power control circuit can modulate the amount of UV projected by a given UV LED by modulating the amount of electricity used to energize the LED. Thus, in contrast to the constant UV emission and energy requirement profiles of a UV fluorescent tube, a UV LED can be "turned up" or "turned down" by increasing or decreasing, respectively, the energy input to the LED.

Figure 4:
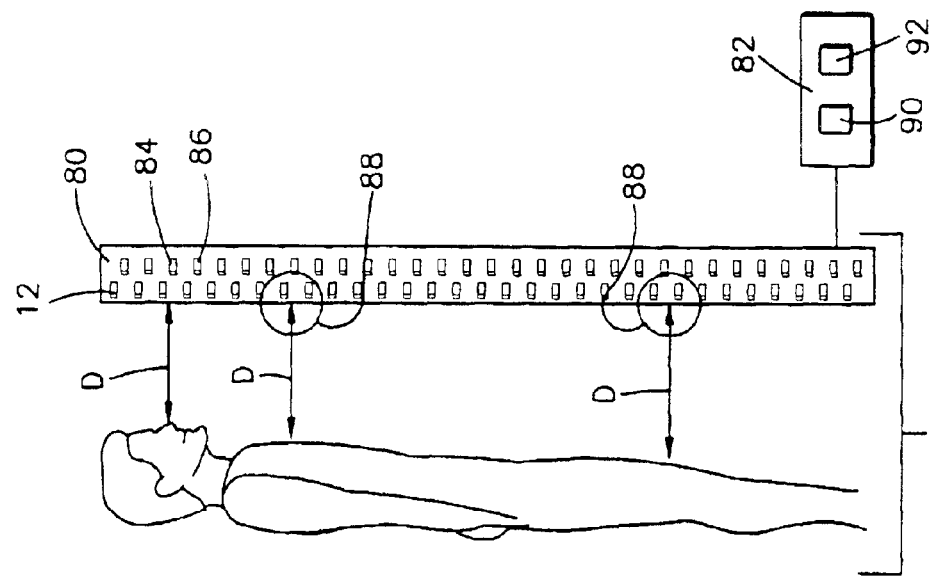
FIG. 4 is a side perspective illustration of another LED UV projection system according to the present invention.

Referring now to FIG. 4, a side view of a rectilinear matrix structure 80 comprising an array of UV LED's 12 is provided in communication with a power and control system 82 according to the present invention. The LED's may comprise UVA LED's 84 and UVB LED's 86. The power and control system 82 may be configured to vary the intensity of all of the UV LED's 12 commonly. It may also increase or decrease the intensities of the UVA LED's 84 relative to the UVB LED's 86 based upon programmed or manual settings and requirements. And/or it may also vary individual LED's 12 intensities, or sub-groups 88 of LED's 12 based upon specific parameters. Examples of parameters include the distance D of skin surfaces from an individual LED 12 or subgroup 88; the region of the body proximate to the an individual LED 12 or subgroup 88 (for example, face regions may indicate lower intensities than leg regions); and desired relative UVA to UVB intensities.

It is preferred that the power and control system may energize LED's for specified time periods. The time periods may be provided by a program, manually set, dynamically altered responsive to input data, or chosen responsive to other system inputs. Exemplary input data may include skin and/or eye complexion parameters, recent session history, amount of UV energy projected in the current session, or other input parameters.

Therefore, a significant advantage of the present invention is the ability to select precise UVA and UVB emission profiles through (1) the selective illumination of individual LED's; (2) varying the UVR output of any given LED by varying its energy input from the power and control system; (3) varying the illumination time period of any given LED; and (4) any combination of these factors. By using UVR LED's with a precision control circuit, the present invention can fine tune the UVA/UVB emission ratios to diminish or even eliminate the premature aging problem associated with the higher UVA/UVB ratios of the prior art tanning bed and booth systems.

Thus, a person with a dark complexion who tans relatively easily may program the system according to the above factors for a relatively short duration of a relatively high UVB to UVA ratio LED illumination. Another person with a fairer complexion may program the device to use a higher UVA to UVB ratio, and select a time period sufficient to cause a desired tanning or health effect, yet brief enough to prevent erythema, premature aging or other undesired effects.

Illumination sessions under the present invention may, therefore, blend different light spectrums including UVA and UVB LED's, over different time periods and intensity levels for each LED utilized. The time periods selected and relative blend of UVA and UVB LED's energized may be from a predetermined menu programmed into the control and power system. These individualized programs may be based upon medical and scientific studies. Accordingly, the best known emission ratio of UVA to UVB may be dynamically selected. If different ratios are subsequently determined by governmental or other health authorities as preferred, than the composite UVA/UVB emission profile may be adjusted to follow the ratios. Similarly, the requirements of people with certain skin complexions, skin and eye-color combinations, or any other predictor may be accommodated by the present invention. Alternatively, or additionally, each user may manually select his own time and UV LED profile.

Is also to be understood that, although the present invention has been discussed with regard to UVA and UVB LED's, other types of LED's may be utilized. Thus, LED's that emit other electromagnetic spectrum light, such as infrared, or any other visible light spectrum, may be utilized with the present invention. The present invention may also be used for applications other than human skin tanning, such as curing applications, "black lights" testing, insect control, and entertainment industry applications, germicidal applications, and therapeutic UVR applications. Therefore, the present invention is not limited to only tanning applications using UVA and UVB LED's, but may be utilized at any type of LED that emits light within a spectrum that will cause a desirable effect. For example, many studies show that artificial light systems may alleviate depression in other seasonal affective disorders (SAD's) that are caused by the reduction in sunlight during the winter months. In some situations, there may be a total lack of natural sunlight such as through habitation of either the Arctic or Antarctic regions during winter months, or prolonged underground or undersea habitation. Thus, alternative embodiments of the present invention may combine UV LED's with other light spectrum LED's, or even other types of lights, such as conventional fluorescent and incandescent lighting.

The embodiment of the invention described above maybe tangibly embodied in a in a computer program residing on a computer-readable medium or carrier 100, illustrated in FIG. 5. The medium 100 may comprise one or more of a fixed and/or removable data storage device such as a floppy disk or a CD-ROM, or it may consist of some other type of data storage or data communications device. The computer program may be loaded into a memory unit 90 to configure a processor unit 92 within the power and control system 82 of FIG. 4 for execution. The computer program comprises instructions which, when read and executed by the processor unit 92 causes the processor unit 92 to perform the steps necessary to execute the steps or elements of the present invention.

While preferred embodiments of the invention have been described herein, variations in the design may be made, and such variations may be apparent to those skilled in the art of tanning beds and booths and other artificial lighting systems, as well as to those skilled in other arts. The materials identified above are by no means the only materials suitable for the manufacture of the present invention, and substitute materials will be readily apparent to one skilled in the art. The scope of the invention, therefore, is only to be limited by the following claims.

What is claimed is:

1. A UVR LED light projection apparatus for irradiating a subject, comprising:
   (a) a plurality of light emitting diodes configured to emit ultraviolet radiation, the plurality of diodes arranged in a matrix corresponding to a shape of the subject to be irradiated; and
   (b) a power modulation control unit in communication with the plurality of diodes;
   wherein the power modulation control unit is configured to energize and cause the diodes to emit light and thereby irradiate the subject with ultraviolet radiation, said ultraviolet radiation having an intensity sufficient to cause material physical change in said subject.

2. The UVR LED light projection apparatus of claim 1, wherein the subject is human skin;
   the material physical change is a tanning of the skin; and
   the amount and type of UVR projected by the plurality of UV LED's may be varied by the power modulation control unit responsive to information input into the power modulation control unit.

3. The UVR LED light projection apparatus of claim 2, wherein the plurality of ultraviolet radiation emitting diodes further comprise UVA light emitting diodes and UVB light emitting diodes, and the power modulation control unit is further configured to select at least one relative intensity ratio of UVA diode intensity to UVB diode intensity.

4. The UVR LED light projection apparatus of claim 3, wherein the power modulation control unit is further configured to energize one or more of the plurality of diodes for at least one time period.

5. The UVR LED light projection apparatus of claim 4, wherein the power modulation control unit is further configured to energize one or more of the plurality of diodes responsive to an input parameter.

6. The UVR LED light projection apparatus of claim 2, wherein the matrix defines an undulating shape corresponding to a shape of a subject.

7. The UVR LED light projection apparatus of claim 2, wherein the matrix is attached to a deformable substrate, wherein the substrate may be deformed to conform to a shape of a subject.

8. A method for irradiating a subject with UVR from a plurality of light emitting diodes, comprising the steps of:
  (a) arranging a plurality of light emitting diodes in a matrix, corresponding to a shape of the subject to be irradiated the plurality of diodes configured to emit ultraviolet radiation;
  (b) providing a power modulation control unit in communication with the plurality of diodes;
  (c) the power modulation control unit energizing and thereby causing the diodes to emit ultraviolet radiation light having an intensity sufficient to cause material physical change in a subject;
  (d) irradiating a subject with said ultraviolet radiation light; and
  (e) the irradiation of the subject with the ultraviolet radiation light causing a material physical change in said subject.

9. The method of claim 8, wherein the subject is human skin;
  the material physical change is a tanning of the skin; and further comprising the steps of:
    inputting information into the power modulation control unit; and
    the power modulation control unit varying an amount and type of UVR projected by the plurality of diodes responsive to the input information.

10. The method of claim 9, wherein the plurality of ultraviolet radiation emitting diodes further comprise UVA light emitting diodes and UVB light emitting diodes, and further comprising the step of the power modulation control unit selecting at least one relative intensity ratio of UVA diode intensity to UVB diode intensity.

11. The method of claim 10, further comprising the step of the power modulation control unit energizing one or more of the plurality of diodes for at least one time period.

12. The method of claim 11, further comprising the step of the power modulation control unit energizing one or more of the plurality of diodes responsive to an input parameter.

13. The method of claim 9, further comprising the step of forming the matrix into an undulating shape corresponding to a shape of a subject.

14. The method of claim 9, further comprising the steps of:
  attaching the matrix of diodes to a deformable substrate; and
  deforming the substrate to conform to a shape of a subject.

15. An article of manufacture comprising a computer usable medium having a computer readable program embodied in said medium, wherein the computer readable program, when executed on a computer, causes the computer to:
  cause a power modulation control unit to energize a plurality of light emitting diodes, arranged in a matrix corresponding to a shape of the subject to be irradiated the diodes thereby emitting ultraviolet radiation having an intensity sufficient to cause material physical change in the subject.

16. The article of manufacture of claim 15, wherein the subject is human skin;
  the material physical change is a tanning the human skin; and
  the computer readable program, when executed on a computer, further causes the computer to cause the power modulation control unit to vary an amount and type of ultraviolet radiation projected by the plurality of responsive data input into computer.

17. The article of manufacture of claim 16, wherein the plurality of ultraviolet radiation emitting diodes further comprise UVA light emitting diodes and UVB light emitting diodes, and the computer readable program further causes the power modulation control unit to select at least one relative intensity ratio of UVA diode intensity to UVB diode intensity.

18. The article of manufacture of claim 16, wherein the computer readable program further causes the power modulation control unit to energize one or more of the plurality of diodes for at least one time period.

* * * * *